(12) United States Patent
Gold

(10) Patent No.: US 10,238,525 B2
(45) Date of Patent: Mar. 26, 2019

(54) TABLE ATTACHMENT APPARATUS

(71) Applicant: Jordan Gold, Aventura, FL (US)

(72) Inventor: Jordan Gold, Aventura, FL (US)

( * ) Notice: Subject to any disclaimer, the term of this patent is extended or adjusted under 35 U.S.C. 154(b) by 813 days.

(21) Appl. No.: 14/867,313

(22) Filed: Sep. 28, 2015

(65) Prior Publication Data
US 2017/0087396 A1 Mar. 30, 2017
US 2018/0326240 A9 Nov. 15, 2018

Related U.S. Application Data

(63) Continuation-in-part of application No. 13/705,272, filed on Dec. 5, 2012.

(51) Int. Cl.
*A61F 5/37* (2006.01)
*A61H 1/02* (2006.01)
*A61H 37/00* (2006.01)

(52) U.S. Cl.
CPC .......... *A61F 5/3769* (2013.01); *A61H 1/02* (2013.01); *A61H 1/0222* (2013.01); *A61H 37/00* (2013.01); *A61H 2201/0119* (2013.01); *A61H 2201/0173* (2013.01); *A61H 2201/0192* (2013.01); *A61H 2201/164* (2013.01); *A61H 2201/168* (2013.01); *A61H 2201/169* (2013.01); *A61H 2201/1619* (2013.01); *A61H 2201/1635* (2013.01); *A61H 2203/0443* (2013.01)

(58) Field of Classification Search
CPC ................ A61G 13/101; A61G 7/0504; A61G 2007/0518; A61G 7/05; A61G 7/0525; A61G 7/0526; A61G 13/10; A61F 5/3792; A61F 5/37; A61F 5/3769; A61F 5/3776; A61F 5/3784; A61B 6/0414; A61B 6/0421; A61B 6/0428; A61H 2201/1619; A61H 2201/1621; A61H 1/0222
USPC ........................ 5/658, 503.1, 424; 128/870
See application file for complete search history.

(56) References Cited

U.S. PATENT DOCUMENTS

| | | | | |
|---|---|---|---|---|
| 2,743,974 | A * | 5/1956 | Black | A61F 5/3776 5/424 |
| 3,313,511 | A * | 4/1967 | Koerner | A61B 6/0421 224/318 |
| 3,580,523 | A * | 5/1971 | Preston | A61F 5/3776 242/378 |
| 3,897,778 | A * | 8/1975 | Forbes-Robinson | A61F 5/3784 128/875 |
| 4,484,571 | A * | 11/1984 | Velazquez | A61B 6/0421 5/601 |
| 4,699,132 | A * | 10/1987 | Carville | A61F 5/3776 128/876 |
| 4,928,360 | A * | 5/1990 | Wilbanks | A61F 5/3776 24/302 |
| 5,048,541 | A * | 9/1991 | Haneline | A61B 6/0421 128/830 |
| 5,433,222 | A * | 7/1995 | Boomgaarden | A61F 5/3769 128/869 |

(Continued)

*Primary Examiner* — Kari Rodriquez

(57) ABSTRACT

A strap attachment apparatus for a treatment table including a spanning belt formed of flexible material secured across opposite sides of said table with a pair of anchors connected at opposite ends of the spanning belt for attachment to the table. The anchors include body strap retainers that support at least one body strap. The body strap is movable on the retainers to adjust the position of the straps to fit a person on the treatment table while the anchors remain fixed to the table.

10 Claims, 4 Drawing Sheets

(56) References Cited

U.S. PATENT DOCUMENTS

2010/0275377 A1* 11/2010 West ..................... A61F 5/3776
5/621
2011/0114102 A1* 5/2011 Hedges ................ A61F 5/3776
128/876

* cited by examiner

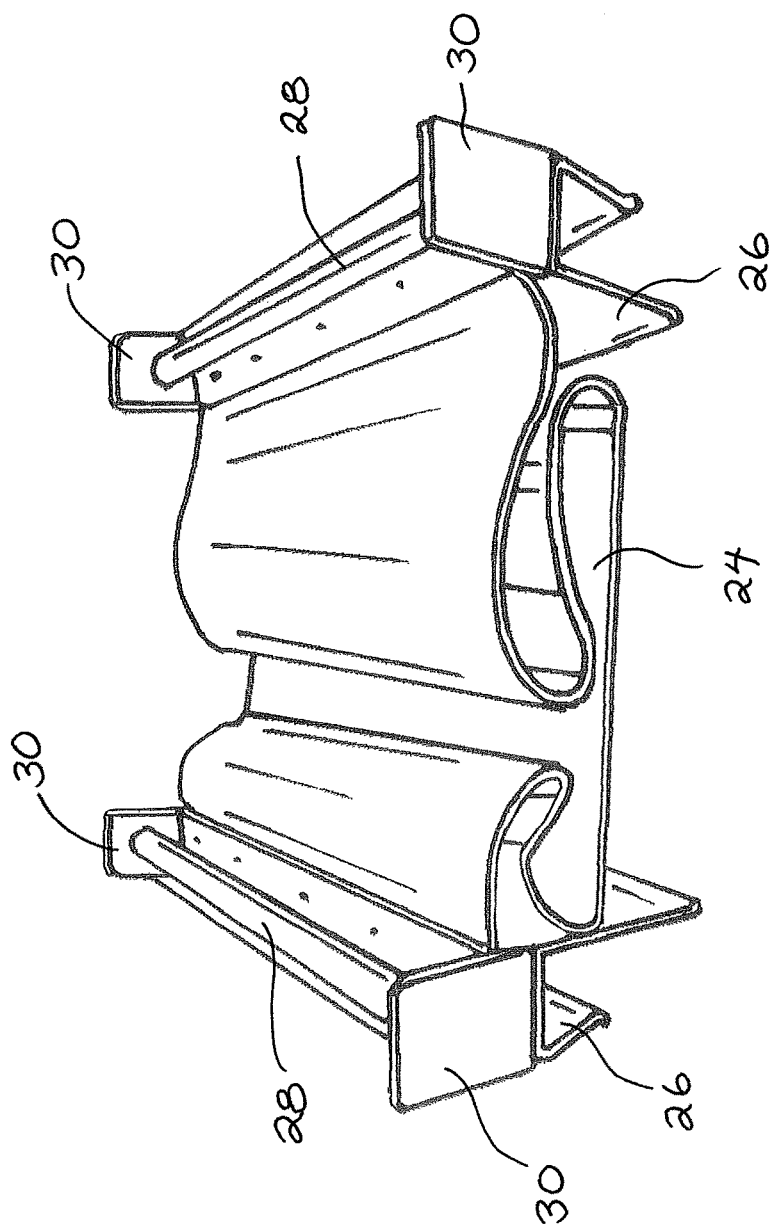

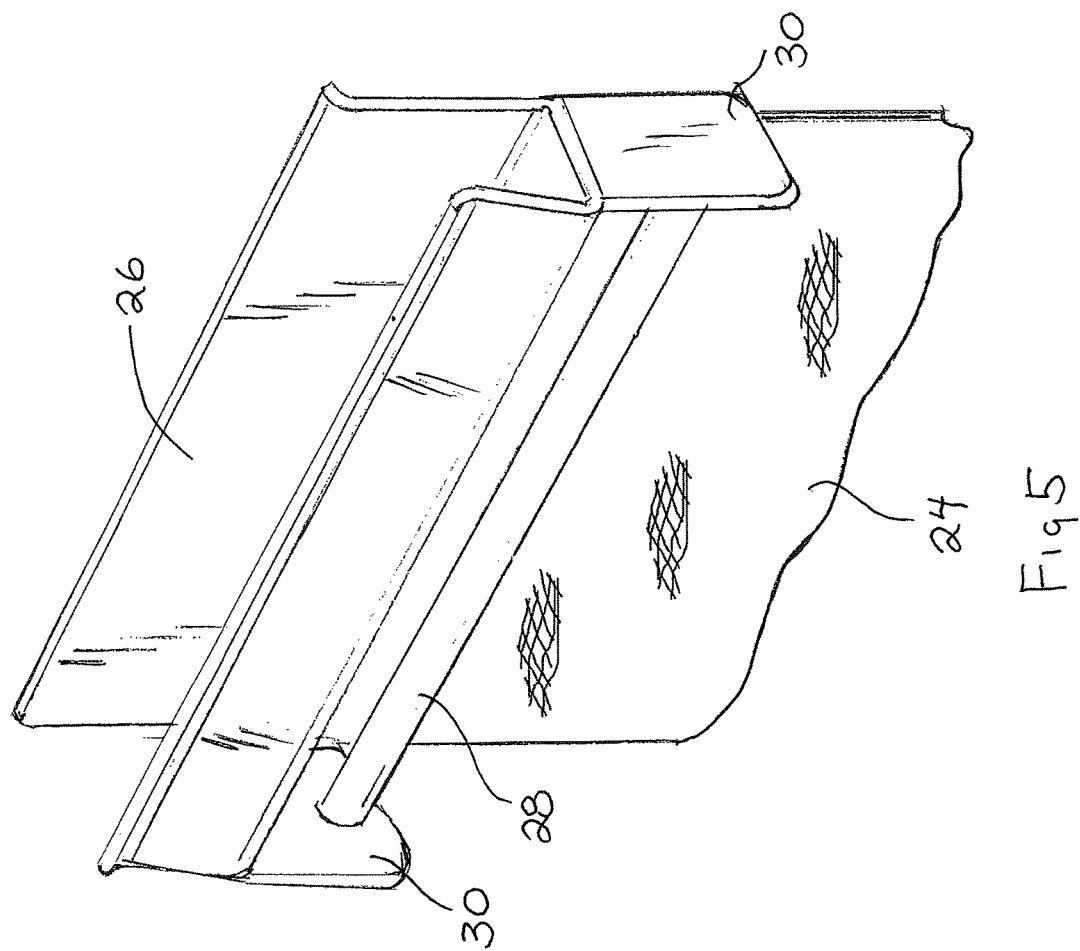
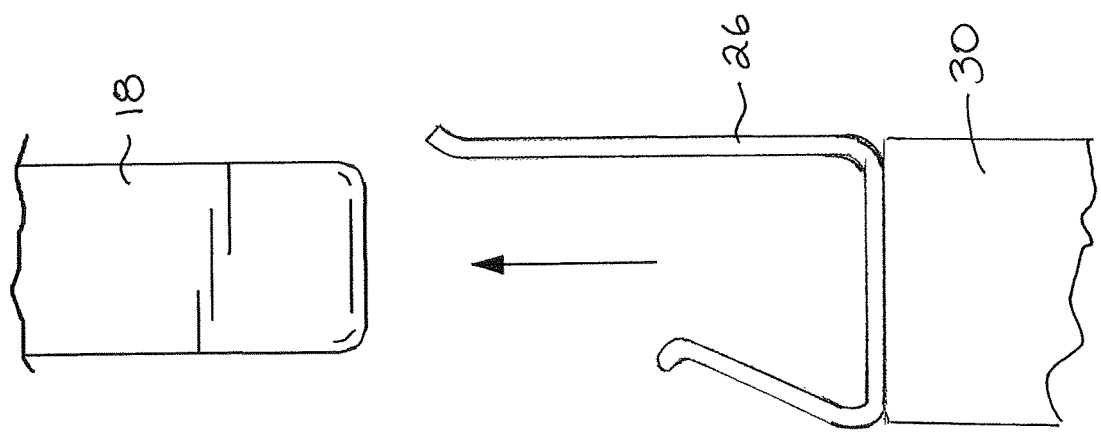

TABLE ATTACHMENT APPARATUS

RELATED APPLICATIONS

The present invention is a continuation in part of application Ser. No. 13/705,272 filed Dec. 5, 2012 titled MASSAGE TABLE ATTACHMENT APPARATUS.

FIELD OF THE INVENTION

The present invention relates to an adjustable strap attachment apparatus for a treatment table to hold a person on the table during stretching manipulations.

BACKGROUND OF THE INVENTION

In order to move efficiently and effortlessly in all ranges and planes of motion as well as perform athletic and similar physical movements, increased flexibility is an asset. This is particularly true as people age. Starting in their thirties and often even much younger, they become slowly and steadily less flexible with an impact on wellness and physical conditioning. Flexibility is lost at a rate of 1% a year whereby it does not take too many years before individuals begin to feel the effects of aging. This becomes a problem for individuals regularly using their athletic abilities, particularly those who perform at an elevated amateur or professional level. In addition, persons with a variety of physical disabilities often find stretching will increase range of movement thereby enhancing life style despite the disability issues.

In order to prevent the loss or decrease of flexibility, the concept of stretching before a physical or athletic endeavor such as playing ball, golfing, dancing and any number of similar physical activities is well known to the participants who engage in these events. Warm-up stretching is commonly done before an event. Also, stretching is incorporated into most serious training programs in order to gain maximum benefit for the performer. In addition to exercises that are done alone by a performer, a wide variety of stretching exercises are used when the performer seeks to work with individuals such as body workers, therapists, trainers and coaches as part of a training protocol. Stretching exercises and manipulations are performed with the aid of an assistant trained to maximize the individual's performance. Specifically, a trainer may move or push an individual's arm or leg to a stretched position to loosen muscle and fascia tissue. This application of force often requires the individual to be grounded or otherwise secured to a support surface to maintain the maximum stretch of a particular limb or body part being worked on without body movement.

Various types of straps and belts have been used to secure an individual to a treatment table in order to maintain the individual in the same position during the stretching force application. A common practice is to wrap straps or belts under the table and around various body parts of the individual being stretched. For example if the legs are being stretched, a strap would likely be placed around the torso or hips of the individual in such a way to allow full movement of the legs while maintaining the torso in a relatively fixed position. Similarly if the individual's arms are to be stretched, it is likely a strap would be placed under the table and around the chest. Whereas these straps do provide some support, they usually are not secured and often move or slide during the application of the stretching force and thereby make the exercise more difficult to control.

The prior art also discloses tables with permanently attached straps that are fixed to the table sides and are designed to wrap over an individual lying on the table to secure the individual in an unmovable, fixed position. Being fixed, this arrangement is limited in adjustability since it does not fit all sizes of individuals who may need the stretching techniques. At best fixed straps require particular individuals to readjust their position with each stretching procedure.

Still another prior art structure for securing an individual in place on a table to facilitate a stretching procedure is formed of a strap having a clip or similar securing device on the end of the strap that is attached directly to the table. A shortcoming of this structure is the requirement of readjusting the location of the strap with each individual procedure and with different sized individuals receiving the work.

SUMMARY OF THE INVENTION

The present invention is particularly adapted for use with the Stretch Zone Method that synthesizes controlled stretching techniques to work with the autonomic nervous system. This method quickly and efficiently improves muscle symmetry, enhances physical performance and mitigates rheumatic pain. The method recognizes the limiting factor to achieving full range of motion is not the length or elasticity of muscles but the nervous control of their tension via the stretch reflex. With precise stabilization, control and comfort, a practitioner systematically positions, stabilizes, isolates and carefully assists each rhythmical stretch. This proprietary method all takes place on innovative tables or tables converted using the present invention. The tables are purposefully designed and adorned with the necessary structure including adjustable belts, pads and straps allowing for the speedy extension of muscles further than the central nervous system would normally permit. As the practitioner continues in this systematic progression, the client's is gently guided past the active range of motion and back to zero tension before the muscle reacts to being stretched by going into further contraction.

Because the technique and the movement required, the practitioner needs a specifically designed treatment table to effectively practice the method. Conventional treatment tables, such as massage tables, do not provide the necessary structure needed. The present invention provides the necessary structure as an attachment apparatus for use with a conventional treatment table, or similar type table that serves as a support for an individual in a prone, supine or side lying position lying on top of the table. The attachment apparatus serves to support and stabilize an individual in a fixed position on the table while undergoing a stretching application of force by a suitable trainer, body worker or physical therapist. The apparatus includes adjustably positioned body straps designed and sized to maintain and secure the person being treated on the table during the application of stretching forces on various body parts. The body straps are adjustably located on a strap support at the table edge that enables the body straps to move laterally along the length of the table edge to secure various sized individuals being treated without moving or readjusting the position of the strap support. The strap support includes a unique positioning and anchoring apparatus integrally formed with the strap support to securely maintain the strap support on the table edge.

The strap support positioning and anchoring apparatus is attached to the table and includes a removable, flexible or elastic belt that is fitted to the upper surface and sized to span the width of the table and permanently secured anchors on opposite ends of the belt for attachment to the edge of the table. The anchors are U-shaped and designed to be attached to opposite sides of the table onto the table side rail frame, preferably under the table out of possible contact with a practitioner conducting the stretching exercises.

The body strap supports are integrally formed with the side rail anchors and include a cylindrical body strap retainer attached to brackets at the ends of the anchors. The body strap retainer is offset from the base of the U-shaped anchors forming an opening between the body strap retainer and the base of the anchor. The length of the cylindrical body strap retainer between the brackets at the ends of the anchors is at least twice the width of the body straps and may have a length that is even longer.

In a preferred embodiment, a body strap or belt that used to support a person lying on the table, is looped around the cylindrical strap retainer in such a way that it extends over the top of the table where it may be secured to a selected body part of the individual to be treated. The length of the cylindrical strap retainer permits the body strap wrapped around the retainer to be adjustably moved along the length of the retainer in order to be precisely located across the selected body part of the individual undergoing the stretch treatment exercise without having to reposition the anchors on the table.

It will be appreciated the body strap or belt attached to the strap bar may be relatively narrow or wider and include various cushioning structures depending upon the manner in which it is used to restrain the individual on the table.

It will also be appreciated that while the present invention discloses two body strap supports, additional supports may be provided. Similarly a single body strap support may be sufficient if the overall length of the body strap support is extended to span a substantial portion of the length of the table. It will be appreciated that several straps or belts may be provided along the length of the support to insure maximum flexibility to accommodate various sized individuals.

The apparatus of the present invention facilitates a stretching treatment from a neurological perspective that re-educates the associated nerve-muscle reflex to enhance the ability to move functionally with a greater range of motion and with less effort. The apparatus of the present invention allows a practitioner to systematically position, stabilize, isolate and manipulate muscles in a scientific way. When a body is properly stabilized such that one segment is fixed, this allows another segment to move without fear into a full stretch. The current apparatus also provides leverage giving the practitioner sufficient control over how intense the stretch becomes and how fast it may be applied. The apparatus also provides isolation such that only the muscles needing stretching are moved eliminating resistance from other muscle groups thereby providing greater control during a stretching treatment. The apparatus also insures proper alignment during the stretching treatment to more easily regulate tension on soft tissues during treatment.

An object of the present invention is the provision of a treatment table attachment apparatus to maintain a person being treated in a fixed position on a massage table.

Another object is the provision of a strap support attached to a treatment table that allows supporting body straps to be adjustable to accommodate a wide variety of different sized individuals being treated on the table.

These and other objects may be understood with reference to the following drawings and descriptive specification.

DESCRIPTION OF THE DRAWINGS

FIG. 4 is a view of the support member detached from a table.

FIG. 5 is a detailed perspective view of one end of the body strap support member.

FIG. 6 is a view of a detail of the apparatus showing the anchor and table side rail.

DESCRIPTION OF THE PREFERRED EMBODIMENT

Figure 1:
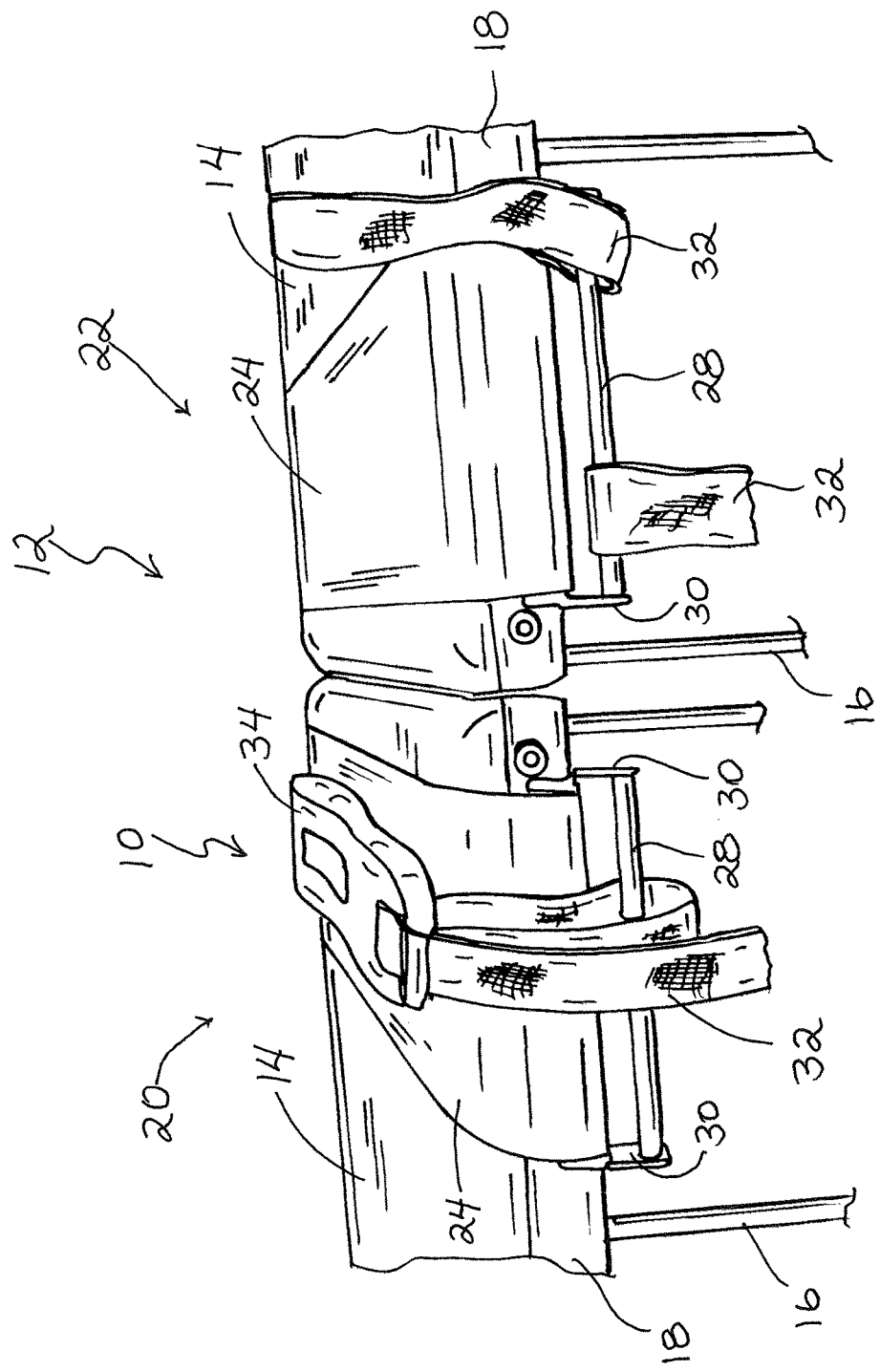
FIG. 1 is a perspective view of the attachment apparatus connected on top of a conventional massage type, treatment table (partially shown) in accordance with the present invention.
Figure 2:
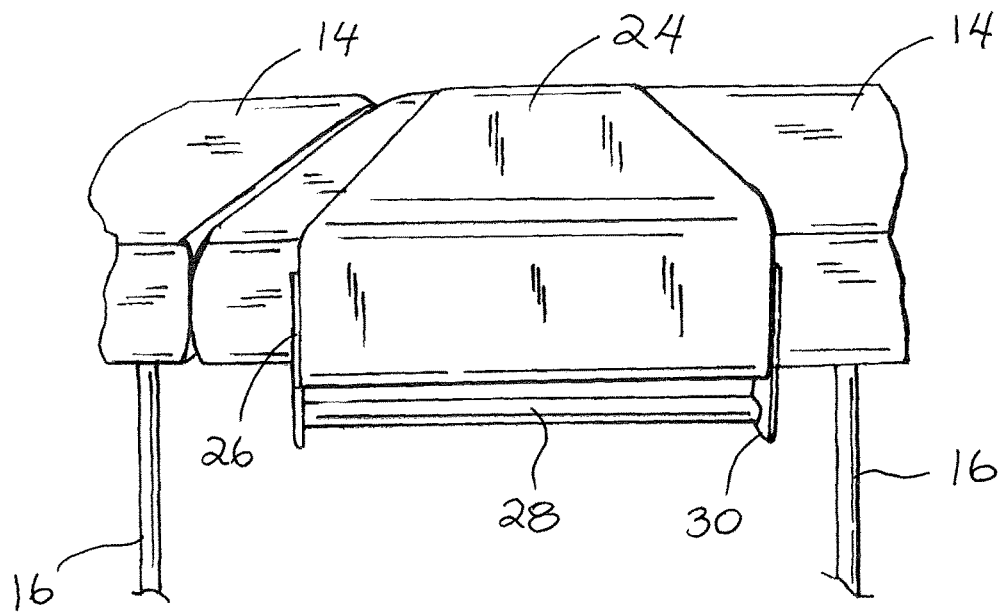
FIG. 2 is a side perspective view of a single body strap support member used on a treatment table without straps.
Figure 3:
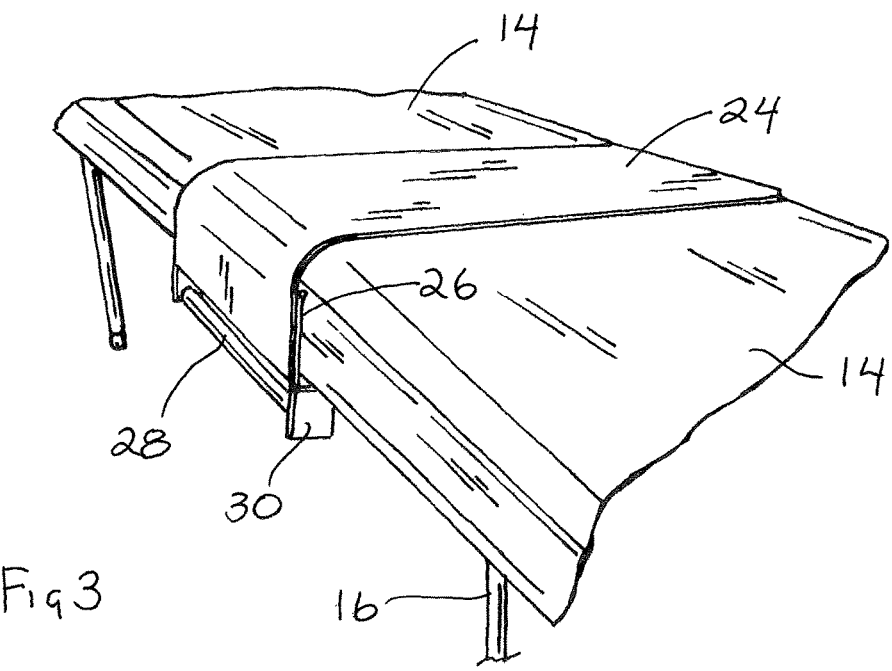
FIG. 3 is an angular perspective view of FIG. 2.

A preferred embodiment of a massage table attachment apparatus 10 in accordance with the present invention is illustrated in the drawings in which like numerals refer to the same parts in each figure. Preferably the attachment apparatus 10 is used in combination with a conventional massage table 12 shown in part including a padded upper surface 14 to accommodate a person lying on the table 12 for treatment, support legs 16 and side rails 18. The version of the massage table 12 shown in the drawings is formed in two sections, an upper body section 20 and a lower body section 22 such that the sections 20 and 22 of the table 12 may be folded together to facilitate carrying and storage.

The attachment apparatus 10 converts a conventional massage table 12 to a table particularly useful for stretching procedures that typically require the application of stretching forces by a trainer or therapist to the person being treated while maintaining the person being treated in a fixed position on the table. The attachment apparatus 10 includes a wide flexible belt 24 that is sized to extend across the upper surface of the padded body support 14 thereby spanning the width of the table 12. Each end of the belt 24 is connected to an elongated, longitudinal, side rail anchor 26 approximately the same width as the belt 24 for attachment to the side rails 18 of the table 12. The ends of the belt 24 are attached to the side rail anchors 26 by suitable fasteners, not shown, or by epoxy type glue, heat welding or other suitable permanently attaching means. The side rail anchors 26 have a generally U-shaped cross section, as shown in the drawings, FIGS. 4, 5 and 6. Preferably the side rail anchors 26 are flexible in order to snap on the side rails 18 of the table 12; see FIG. 6. Alternately the anchors 26 may be rigid and sized to snugly fit over the side rails 18. The flexible spanning belt 24 exerts tension on the side rail anchors 26 to insure they remain in place during use.

The side rail anchors 26 are integrally formed with a body strap retainer 28 supported by a pair of brackets 30 that are formed with and extend from the ends of the side rail anchors 26. Preferably each body strap retainer 28 is a rigid cylindrical rod or tube having opposite ends attached to the brackets 30. Each body strap retainer 28 is designed to adjustably support at least one body support strap 32. The overall length of a body support strap retainer 28 is at least twice the width of the body support strap 32 positioned thereon enabling the body strap 32 to be adjustably moved along the length of the retainer 28 to accommodate different sized individuals with having to remove and reposition the entire attachment apparatus 10. In this regard, it will be appreciated that the retainer 28 may be several times longer than the width of the supported body strap 32, as for example shown in FIG. 1 of the drawings.

In the preferred embodiment illustrated, the body strap retainer 28 is positioned directly under the side rail anchors 26 however the body strap retainer 28 may be angularly offset further under the table 12 and function equally as well.

Preferably, the body support straps 32 are attached to the table 12 by being looped over the cylindrical body strap retainer 28 and extend across the table 12 to support a person lying thereon during a physical therapy or similar stretching session. The body support straps 32 can be provided in a variety of widths and sizes, the only restriction being that they have a width no greater than half the length of the retainer 28 to facilitate adjustably positioning the body strap 32 along the retainer 28. Referring to FIG. 1, a body support strap 32 designed to engage the torso or upper body of the person being worked on, is provided with a cushion 34 to more comfortably spread the retaining forces of the strap 32 against the body of the person on the table 12.

As previously indicated, the width of the body support straps 32 is considerably less than the length of the cylindrical retainer 28 such that the body support straps 32 may be longitudinally positioned along the length of the retainer 28 in order that the straps 32 can be adjusted to the physical characteristics of the person being treated without the necessity of removing and repositioning the entire apparatus 10. This arrangement also permits a plurality of straps to be positioned on a single cylindrical retainer 28 as shown 28 on the section 24 of the table 12 in the drawings.

In use, the massage table attachment apparatus 10 of the present invention is attached to a massage table 12 by spreading the spanning belt 24 across the width of the upper surface 14 of the massage table 12. The open ends of the U-shaped, side rail anchors 26 are pushed over and snapped onto the downwardly extending side rails 18 of the table 12. Once the anchors 26 are frictionally attached to the side rails 18, they are maintained thereto by the tension of the belt 24. The body support straps 32 are adjustably positioned over the cylindrical retainer 28 by looping a strap 32 through the opening between the cylindrical retainer 28 and the bottom of the anchor 26. A person being treated lies on top of the table 12 and the body support straps 32 are secured to a selected body part to maintain the person on the table 12 in a fixed position during treatment. The number of straps 32 used and the location on the body of the person being treated are determined by the size of the individual and the particular body work/stretching techniques or exercises that are suited for the particular individual being treated.

Whereas the apparatus has been shown as a specific size relative to the table, it will be appreciated that modifications of the attachment apparatus may be made. For example, the overall length of the strap attachment apparatus may vary depending upon the intended use and may extend the entire length of the side of a massage table in order to accommodate a number of body support straps. In addition, the body support straps may be connected to the retainers by mechanical means rather than being looped over the retainers.

Other modifications may be made to the above described apparatus in keeping within the spirit and scope of the present invention, as defined in the following claims.

The invention claimed is:

1. A strap attachment apparatus for a table having a support surface, sides and side rails comprising:
a spanning belt formed of flexible material having a length to be secured across opposite sides of said table;
a pair of elongated, spanning belt attachment anchors at opposite ends of said spanning belt; said anchors being structured and sized to fit and to engage said side rails at said opposite sides of said table to attach said spanning belt to said table;
said spanning belt attachment anchors further including integrally formed body strap retainers; said body strap retainers having a length extending along the length of said anchors;
and, at least one separate body strap having ends attached to and movably positioned on each of said body strap retainers; said body strap having a width less than the said length of said body strap retainers such that said length of said body strap retainers is at least twice the width of said body strap; said length of said body strap retainers and said width of said body strap permitting longitudinal, adjustable movement of said body strap along said length of said body strap retainers while the anchors remain attached to the table and said body strap remains attached to said body strap retainers to adjust the position of the body strap to fit a person on the treatment table.

2. The apparatus of claim 1 wherein said anchors are defined as being generally U-shaped and further including mounting brackets integrally formed with and extending from ends of said U-shaped anchors.

3. The apparatus of claim 2 wherein said body strap retainers are cylindrical rods attached to said mounting brackets.

4. The apparatus of claim 2 wherein said U-shaped anchors are further defined as being flexible for engagement of said table.

5. The apparatus of claim 1 wherein said ends of said body strap are further defined by being formed as a loop positioned over each of said body strap retainers.

6. The apparatus of claim 1 further including a plurality of body straps on said body strap retainers.

7. A strap attachment apparatus for a treatment table having an upper surface, side rails and a support comprising:
a spanning belt formed of flexible material having a length to be secured across opposite sides of said table;
a pair of elongated, spanning belt attachment anchors at opposite ends of said spanning belt; said anchors being structured and sized to fit and to engage said side rails at said opposite sides of said table to attach said spanning belt to said table;
said spanning belt attachment anchors further including support brackets at each end thereof and body strap retainers attached to said support brackets and further defined by having a body strap retainer length extending between said support brackets at the ends of said anchors;
and, at least one separate body strap having ends attached to and movably positioned on each of said body strap retainers; said body strap having a lesser width than the said body strap retainer length such that said length of said body strap retainers is at least twice said width of said body strap; said length of said body strap retainers and said lesser width of said body strap permitting longitudinal, adjustable movement of said body strap along said length of said body.

8. The apparatus of claim 7 wherein said body strap retainer is a cylindrical rod.

9. The apparatus of claim 7 wherein said spanning belt attachment anchors are U-shaped and sized to fit over and engage said side rails.

10. The apparatus of claim 7 wherein said body strap retainers extend the entire length of said anchors.

* * * * *